United States Patent
Paluch

[11] Patent Number: 5,988,164
[45] Date of Patent: Nov. 23, 1999

[54] BREATHING CIRCUITS WITH HUMIDITY CONTROLS

[76] Inventor: Bernard Paluch, 1607 Cedar La., Mount Prospect, Ill. 60056

[21] Appl. No.: 08/509,078

[22] Filed: Jul. 31, 1995

[51] Int. Cl.$^6$ .................................................. A61M 16/00
[52] U.S. Cl. ............................... 128/203.26; 128/204.17
[58] Field of Search ........................ 128/203.26, 203.27, 128/204.17, 911

[56] References Cited

U.S. PATENT DOCUMENTS

| | | | |
|---|---|---|---|
| 379,952 | 3/1888 | Gold | 128/911 |
| 3,898,978 | 8/1975 | Marcus | 128/204.17 |
| 3,912,795 | 10/1975 | Jackson | 128/911 |
| 4,013,122 | 3/1977 | Long | 128/204.17 |
| 4,333,451 | 6/1982 | Paluch . | |
| 4,355,636 | 10/1982 | Oetjen et al. | 128/204.17 |
| 4,589,409 | 5/1986 | Chatburn et al. | 128/203.26 |
| 4,773,410 | 9/1988 | Blackmer et al. | 128/203.26 |
| 4,829,997 | 5/1989 | Douwens et al. | 128/203.26 |
| 4,967,744 | 11/1990 | Chua . | |
| 5,121,746 | 6/1992 | Sikora | 128/911 |
| 5,163,423 | 11/1992 | Suzuki | 128/203.26 |
| 5,309,906 | 5/1994 | LaBombard | 128/911 |
| 5,375,948 | 12/1994 | Eilentropp . | |
| 5,377,670 | 1/1995 | Smith | 128/911 |
| 5,431,157 | 7/1995 | Mourkidou et al. | 128/203.12 |
| 5,537,996 | 7/1996 | McPhee | 128/204.17 |
| 5,558,084 | 9/1996 | Daniell et al. | 128/204.17 |
| 5,701,887 | 12/1997 | Rustad et al. | 128/911 |

OTHER PUBLICATIONS

U.S. Department of HHS, "FDA Safety Alert—Hazards of Heated–Wire Breathing Circuits", Jul. 14, 1993, Washington, DC.

*Primary Examiner*—Aaron J. Lewis
*Attorney, Agent, or Firm*—Walter C. Ramm

[57] ABSTRACT

Breathing circuits for medical respiratory devices which have an inspiratory conduit for delivery of respiration-related aeriform substances to a patient, may also have a expiratory conduit, and, in any case are arranged to communicate with a patient interface, such as a wye (14), and have heating means for respiration-related aeriform substances in at least the inspiratory conduit. The heating means may be a heated-liquid heating tube (11) within at least the inspiratory conduit or an electrical heating wire (38) on or in an inspiratory conduit comprising respiratory hose (37). The tube is in circulatory relationship with a heated-liquid reservoir (13) and is arranged internally to contain heated liquid (30) from the reservoir, and to transfer heat from the liquid—by radiation and conduction from the tube wall—to the substances in the conduit. This transferred heat tends to inhibit or to control formation of dangerous aqueous condensate from the substances by compensating heat losses they otherwise sustain, enhancing their capacity to retain water vapor and providing an intra-conduit environment in which the condensate is unlikely to form. A manifold (12) enables the tube to extend to the expiratory conduit.

11 Claims, 4 Drawing Sheets

BREATHING CIRCUITS WITH HUMIDITY CONTROLS

BACKGROUND OF THE INVENTION

This invention relates to respiratory apparatus and, in particular, to breathing circuits with capability for maintaining humidified status of aeriform substances therein in order to inhibit or to control formation of condensate from the substances.

Respiratory apparatus is familiar in medicine and surgery for ventilation and therapy of the lungs, administration of anesthetics and other medicaments, and other procedures. The breathing circuit of exemplary respiratory apparatus, such as a mechanical pulmonary ventilator, implements delivery and exchange of aeriform substances for and from the patient by way of inspiratory and expiratory channels. Each channel provides a flow path enclosed by wall portions of a conduit and of a patient interface which, commonly, is a shaped tubular wye piece. The conduit may be a flexile hose or hose-like article. The wye piece has an inspiratory airway as the delivery end of the inspiratory flow path, an expiratory airway as the beginning of the expiratory flow path, and a third airway common to the other two. The wye piece may be joined with an endotracheal tube, a tracheostomy tube, or a face mask on the patient.

The background for this invention includes these points:

(a) A pulmonary ventilator, as an exemplary respiratory device, has a breathing circuit and a humidifier. The humidifier is up-path of the breathing circuit and serves to raise the temperature of and add water vapor to aeriform substances destined for the patient.

(b) Aeriform substances in the breathing circuit are likely to sustain heat losses to walls of the circuit's conduits. The losses decrease the capacity of the substances to retain water vapor.

(c) The ventilator does not provide means downpath of the humidifier for increasing absolute volume of water vapor in aeriform substances in its breathing circuit.

Safe and effective operation of a breathing circuit requires proper humidification and heating of aeriform substances delivered by the circuit. If water vapor in the substances in a conduit of the circuit reaches saturation level as a result, for example, of heat losses noted in point (b), aqueous condensate is likely to form. This condensate is recognized as hazardous and potentially fatal because, as it pools or accumulates, it harbors infective agents, may be inhaled by the patient, and may obstruct or occlude the inspiratory conduit thus restricting delivery of the substances and imposing increased labor of breathing on the patient.

Various products and methods have been proposed to deal with unwanted effects and liabilities of such condensate. My U.S. Pat. Nos. 3,865,106 and 3,945,378, and other patents, relate to breathing circuits in which the inspiratory conduit, to reduce heat loss therefrom, is coaxial with and located within the expiratory conduit. My U.S. Pat. No. 4,333,451 teaches closed-system condensate removal from breathing circuits. U.S. Pat. No. 4,967,744, to James Chua, discloses a breathing circuit with a coaxial arrangement of conduits and an electrical heating wire on the inspiratory conduit. U.S. Pat. No. 5,357,948, to Heinz Eilentropp, which is hereby incorporated by reference, discloses heatable respiratory hose with a heating wire or conductor on the outside of the hose and a connection to an electric power supply. Some such devices, products and methods are in service.

Electrical heating wires immediately proximate flammable or combustion-supporting inhalants, or aqueous condensate, may have unwanted safety implications. A regulatory alert was issued in 1993 because of safety problems reported in connection with electrical heating wires in ventilator breathing circuits. Accordingly, need continues for means and methods safely to control relative humidity and to inhibit and control condensate formation in breathing circuits.

SUMMARY OF THE INVENTION

In this summary and elsewhere in this specification

"aeriform substance" means a respiration-related aeriform substance or product, such as an inhalant or an exhalant, including air, oxygen ($O_2$), water vapor, a gas-vapor mixture, aerosols and the like, in gaseous, vaporous or air-like phase.

"condensate" means a substance or product in liquid or aqueous phase including a product or substance in course of formation or condensation, or as formed and condensed from, an aeriform substance in a breathing circuit.

"rh" abbreviates relative humidity as conventionally defined and, in the technical literature, represented by the symbol $H_R$.

The general object of this invention is in aid of safe and effective utilization of respiratory devices, in the interests of patients and care givers, by inhibiting or controlling formation of condensate from aeriform substances in breathing circuits. Within the general object, specific objects include controlling rh of the substances as they transit the circuit, an interior heating tube for a circuit, and avoidance of problems that attend electrical heating wires in close proximity to flammable or combustion-supporting substances in a circuit.

To accomplish these objects, this invention provides a liquid-based heating tube in at least the inspiratory conduit of a breathing circuit, and may include automated controls for the tube. These controls may, as well, serve other heating means for the conduit.

The heating tube is arranged internally to receive heated liquid. A portion of the tube is within the inspiratory conduit. Thus, when aeriform substances are in movement in the conduit and heated liquid is in the tube, heat exchange occurs. Heat from the liquid transfers—at least by radiation and conduction from the tube wall—to the conduit interior and to the substances. This heating confers one or more of rh-related advantages or benefits: a compensatory effect for heat losses the substances otherwise sustain, enhanced capacity of the substances to retain water vapor, and intra-conduit environment tending to inhibit formation of condensate from the substances.

The heating tube may serve both inspiratory and expiratory conduits, and may combine or cooperate with other means to supply heat to or to affect rh of aeriform substances in a breathing circuit, including—subject, otherwise, to appropriate conditions—an electrical heating wire of the type described.

The invention may include a sensor to monitor rh levels of aeriform substances in the breathing circuit and to signal a high such level so, in response to the signal, heat may be furnished to the substances by the heating tube or by such other heating means for the conduit. In the case of the heating tube, heat is supplied by actuating a pump to circulate heated liquid through the tube.

REFERENCE NUMERALS AND CHARACTERS

In the drawings and in this specification these reference numerals and characters indicate and identify apparatus, elements, features and aspects of and with reference to this invention:

numeral 1 is a breathing circuit with a heating tube.
numeral 2 is a breathing circuit with a heating tube and automated rh controls.
numeral 3 is a breathing circuit comprising automated rh controls as in circuit 2 and an electrical heating wire.
numeral 4 is a ventilator as an exemplary respiratory device.
INS is an inspiratory conduit of a circuit.
EXP is an expiratory conduit of a circuit.
AER indicates aeriform substance(s).
In circuit 1, as indicated, and in circuit 2
11 is a heated-liquid heating tube.
12 is a manifold.
13 is a reservoir.
14 is a wye piece.
15 indicates the inspiratory airway of wye 14.
16 indicates the expiratory airway of wye 14.
17 is a first inspiratory hose.
18 is a second inspiratory hose.
19 is a first expiratory hose.
20 is a second expiratory hose.
21 is a water heater for reservoir 13.
22 is the inspiratory side of manifold 12.
23 is the expiratory side of manifold 12.
24 is the transverse member of manifold 12.
25 is the common wall of manifold 12.
26 indicates a first or up-path port.
27 indicates a second or down-path port.
28 indicates a third or inter-conduits port in wall 25.
29 is a pump including motor and power connection.
30 indicates water as exemplary liquid.
In circuit 2, as indicated, and in circuit 3
31 is an rh sensor.
32 is an assembly comprising wye 14 and sensor 31.
33 is a housing for sensor 31.
34 is the probe of sensor 31.
35 is a controller.
36 is an electrical cable.
37 is respiratory hose.
38 is an external electrical heating wire on hose 37.
39 is a connector/power source for wire 38.
In and of device 4
41 is the humdifier.
42 is the exhalation valve.
As accessories with reference to tube 11
51 is a tube clip.
52 is a strut.
53 is the ring or annulus of strut 52.
54 is the aperture within ring 53.
55 is an arm of strut 52.

DETAILED DESCRIPTIONS OF THE INVENTION

Embodiments and methods of this invention, in their several elements and aspects, including structure and operability, and according to these descriptions, represent preferred embodiments of and best modes of the invention. In some elements and aspects, an embodiment of this invention may be an improvement of or with reference to breathing circuits otherwise known to the art.

Circuit 1

Figure 1:
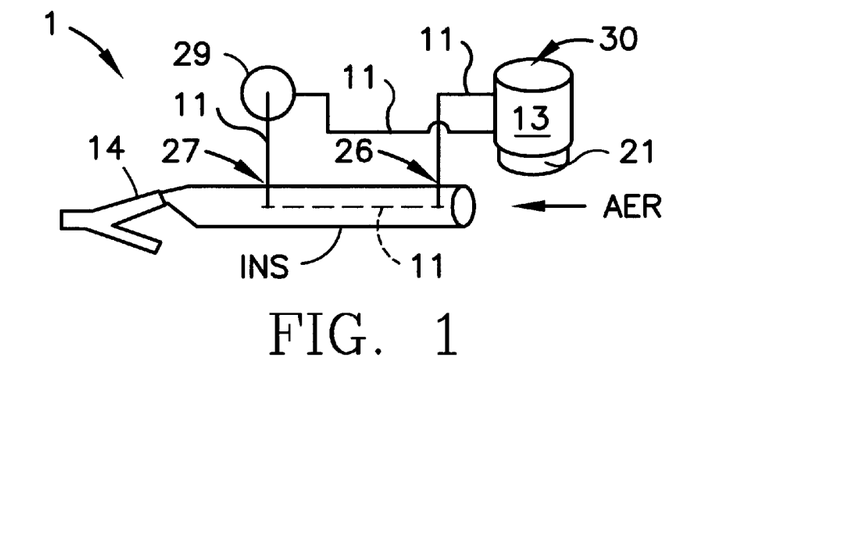
FIG. 1 is schematic diagram of a breathing circuit with a heating tube within the inspiratory conduit of the circuit.

FIG. 1 discloses circuit 1 as a generalized heating-tube breathing circuit with exemplary structural elements and operational aspects. The circuit includes tube 11, reservoir 13, and conduit INS which is in communication with wye 14 and has wall portions defining the inspiratory flow path and ports 26 and 27. The conduit may be conventional respiratory hose with annular cross section and minimum inner diameter of 0.75 inch or 20 mm. Substances AER—from, say, a pulmonary ventilator—are in movement on the flow path toward the down-path end of the conduit and the wye.

Tube 11 is flexile and in circulatory relationship with reservoir 13. The tube transits the wall of conduit INS via ports 26 and 27, and is of sufficient length to provide the circulatory relationship and so that, according to spacing of those ports, a substantial portion of the tube is in generally lengthwise orientation within the conduit and there directly exposed to the inspiratory flow path.

Tube 11 may be polyethylene material and, typically, is cylindric with outer diameter of, say, 0.25 inch or 7 mm., and uniform wall thickness in the range of 0.012–0.035 inch or 3.5–10 mm. In any case, this outer diameter is less than the corresponding inner diameter of conduit INS, and the portion of the tube within the conduit allows free passage of substances AER along the inspiratory flow path and is in or may approach concentricity with the conduit wall except near ports 26 and 27. A small fitting, such as a grommet at each port, fixes the tube there, assures sealed status of the port, and mechanically accommodates the tube's transit of the conduit wall.

Reservoir 13, with associated heater 21, serves tube 11 as a source of heated liquid medium such as water 30. The reservoir is sited near conduit INS; is vented, insulated and otherwise suited for such service, and may be fabricated of aluminum. Water supplied to the tube is at substantially higher temperature—say, in the range of 150–160° F.—than substances AER. The heater may be an electric cartridge heater. Reservoir and tube together form a heated water containment with exemplary capacity in the 60–150 ml. range.

The wall of tube 11 is well suited for heat transfer. As pump 29 delivers heated water 30 to the tube, and substances AER are in movement in conduit INS, heat from the water transfers across the tube wall to the substances. This heating tends to lower and to control the rh level of the substances, and confers one or more of the noted benefits and advantages.

Circuit 1 is suitable for breathing circuits, respiratory devices and similar applications where heating within conduit INS suffices for condensate inhibition or control, or capacity of substances AER in an expiratory conduit to carry water vapor is of lesser concern.

Circuit 2

Figure 2:
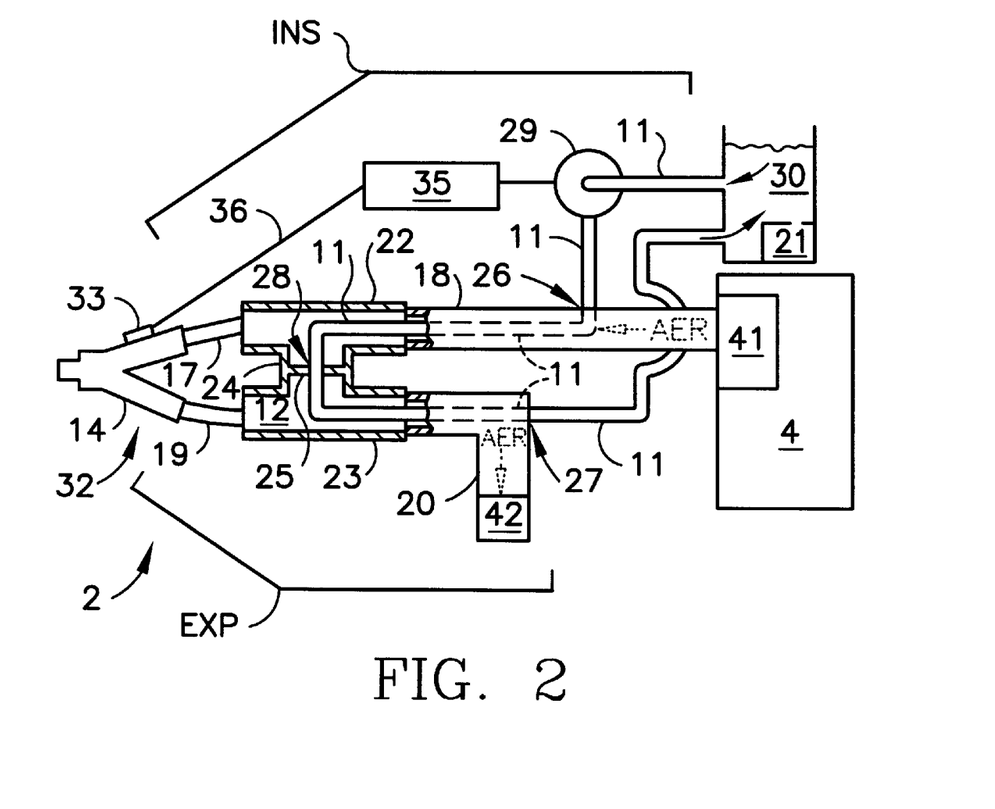
FIG. 2 is a schematic diagram of breathing circuit with a heating tube within the inspiratory and expiratory conduits, and automated controls including a wye-sensor assembly. Portions of the conduits and manifold are as removed to show the route of the tube.

FIG. 2 discloses circuit 2 with tube 11, manifold 12, reservoir 13 and associated heater 21, wye 14, pump 29, discrete conduits INS and EXP, and automated controls with reference to the humidity of substances AER in conduit INS. Conduit INS extends between humidifier 41 and airway 15, and includes hose 18, side 22 of the manifold and hose 17. Conduit EXP extends between the expiratory airway of the wye and valve 42, and includes hose 19, side 23 and hose 20. Each conduit comprises wall portions defining its channel or flow path. Hose 18 defines port 26. Hose 20 defines port 27. The manifold defines common wall 25 and an inter-conduits course via the manifold and port 28 in the common wall.

In circuit 2, tube 11 has a circulatory route from/to reservoir 13 and, on the inter-conduits course, transits port 26 into and runs interiorally of hose 18, transits port 28 within manifold 12, runs interiorally of and transits port 27 from hose 20. The tube may have somewhat greater length than the heating tube of circuit 1 because it is in both conduits and makes a "U" turn, but in other respects it has essentially the same characteristics as the tube of circuit 1. A substantial portion of the tube is within each conduit, may be in near-concentric relationship with the wall portions of the conduit except in the area of each port, and is exposed to the flow path or channel of the conduit. Again, the tube does not affect free passage of substances AER, and a grommet or like fitting may accommodate the tube at and around port 26 and port 27.

Automated controls of circuit 2 include sensor 31 on wye 14, and controller 35. The sensor is arranged to monitor airway 15. The sensor and wye comprise assembly 32 (see FIGS. 5–6) which is, of course, a patient interface member.

Figure 3:
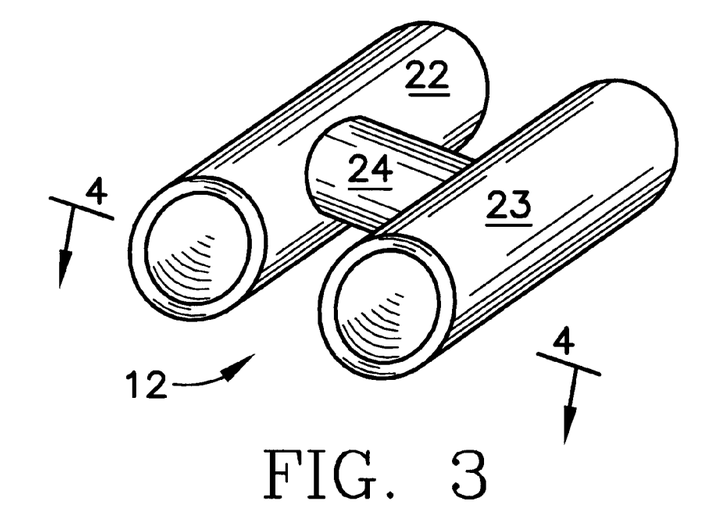
FIG. 3 is a perspective view of the manifold.
Figure 4:
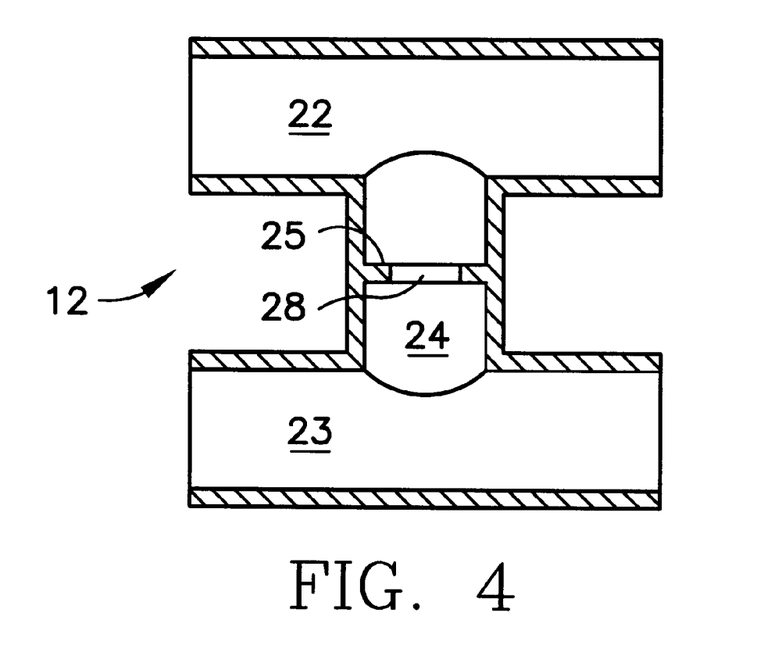
FIG. 4 is a sectional plan view of the manifold along line 4—4 of FIG. 3.
Figure 5:
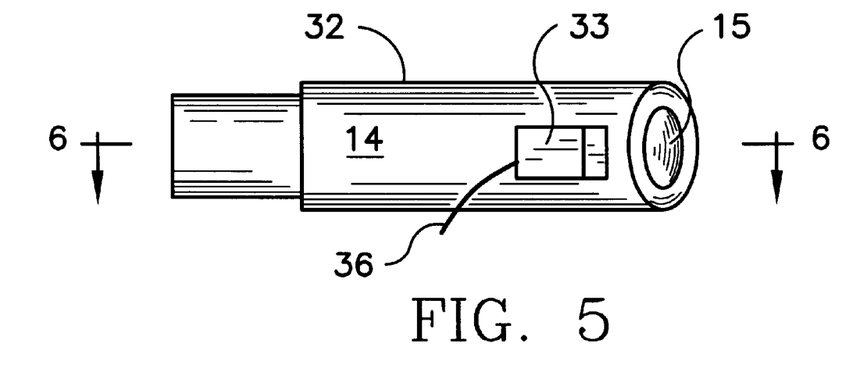
FIG. 5 is a plan view of the wye-sensor assembly.

FIGS. 3–4 are respective exterior and interior depictions of exemplary manifold 12. The manifold is "H"-like with sides 22 and 23 and cross member 24 which, typically, are tubular, substantially rigid wall portions, and may be formed of plastic materials. Each side has an up-path and a down-path opening. FIG. 4 looks toward the down-path opening of side 22 and up-path opening of side 23. FIG. 5 enlarges the view of the manifold in FIG. 2. Port 28, as the inter-conduits or inter-channels port, corresponds to and is not larger than the cross section of tube 11. The manifold may but need not be a unitary structure.

Referring, again to FIG. 2, manifold 12 defines hoses 17 and 19 as "proximal" and hoses 18 and 20 as "distal" with reference to assembly 32, and serves as tube-reversal means and to keep hoses and tube kink-free in the area of the "U" turn. The manifold and assembly 32 are close to each other; ideally, they should be separated by not more than 6 inches or 150 mm. (inclusive of the proximal hoses). As bracketed by the manifold, conduits INS and EXP may be generally parallel over portions of their lengths.

Tube 11 may be installed in manifold 12 by introducing one end of the tube into an up-path opening, leading the end close to port 28, drawing the end through the port (if and as necessary) by a implement such as pliers or forceps, and pulling the tube through and out of the manifold via the down-path opening of the other side; alternatively, the manifold may be constructed to accommodate other methods of installation. In any case, with the tube installed in the manifold to occupy and close port 28, wall 25 prevents cross-flow between the conduits. The manifold and hoses are conventionally joined after tube 11 is installed. The distal hoses are conventional and, preferably, transparent, flexile, crush resistant and of annular cross section; may be corrugated; and, like conduit INS of circuit 1, each has minimum inner diameter of, say, 0.75 inch or 20 mm. The proximal hoses may be transparent and are otherwise adapted suitably to communicate between the manifold and assembly 32.

Reservoir 13 is proximate device 4 and the distal hoses, and otherwise may be as described for circuit 1. Heater 21 may be conventionally arranged automatically to operate to heat water 30 in the reservoir to a temperature in the 150–160° F. range, but to cut off at a higher temperature.

Figure 6:
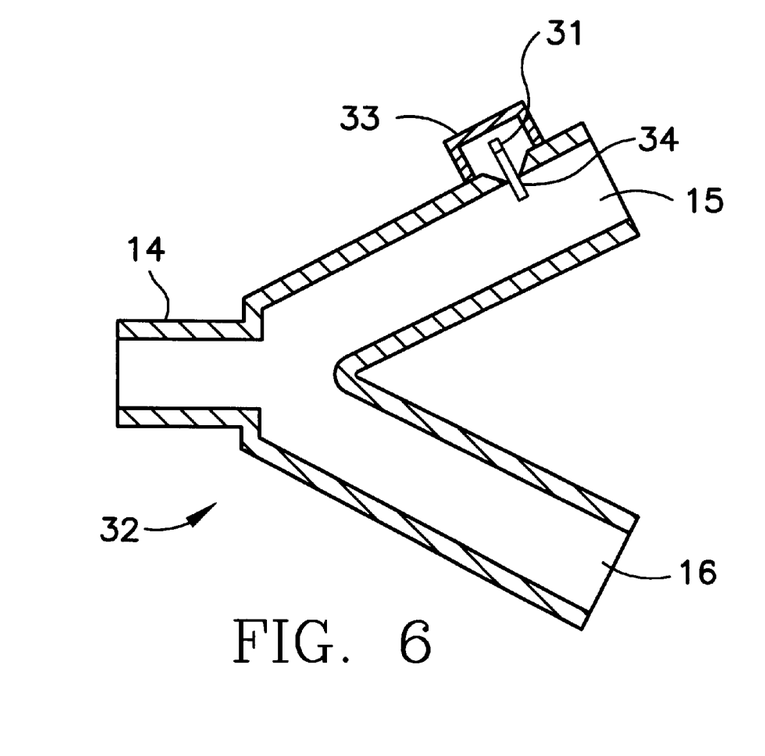
FIG. 6 is a sectional elevation view of the wye-sensor assembly along line 6—6 of FIG. 5.
Figure 7A:
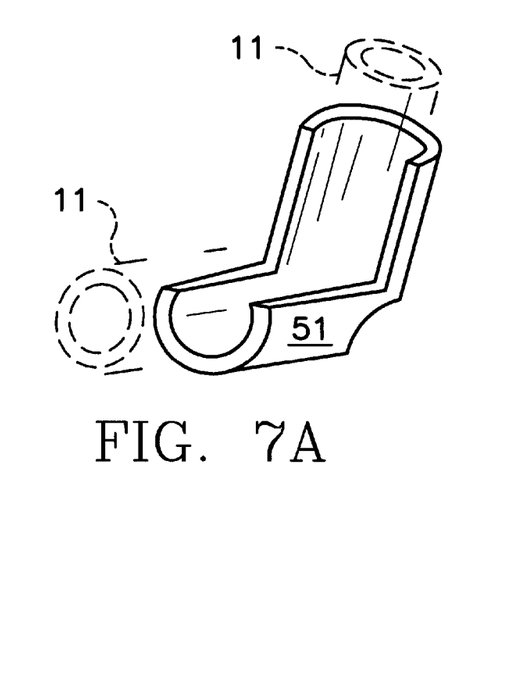
FIG. 7A is a perpsective sketch of a clip as an optional accessory for providing a bend in the heating tube. A short length of tube, in phantom, is in the clip.
Figure 7B:
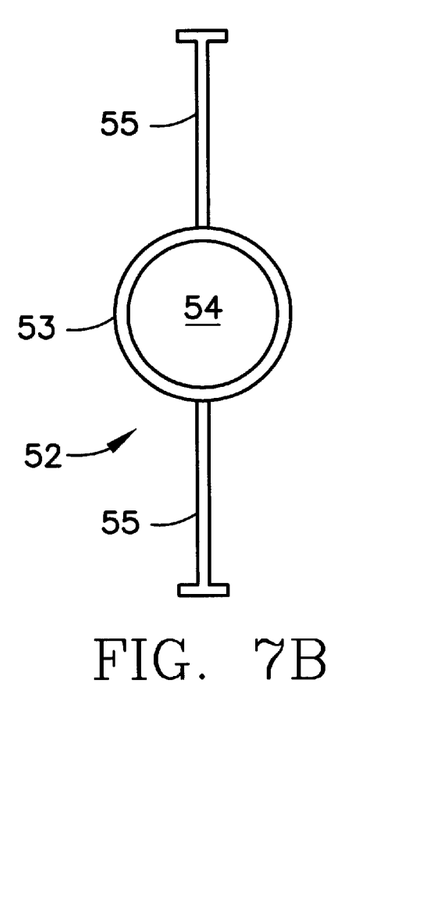
FIG. 7B is a end-view elevation of a strut as an optional accessory for spacing the heating tube from the conduit wall.
Figure 8:
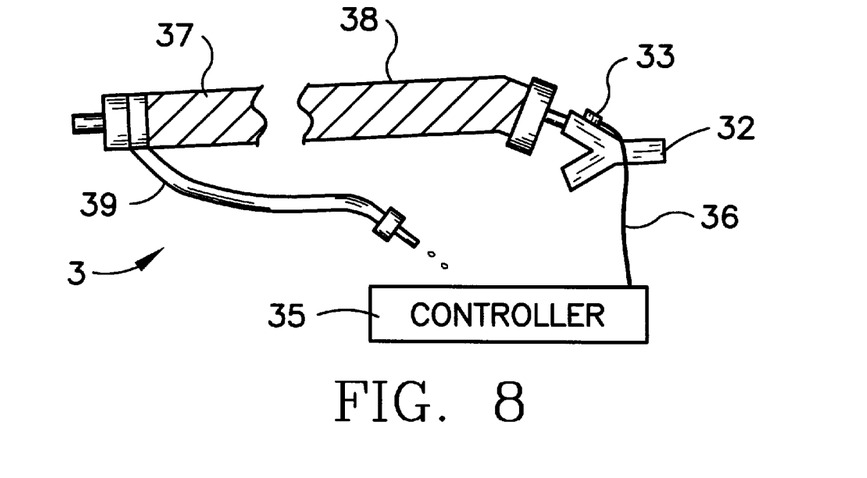
FIG. 8 is a schematic diagram of a breathing circuit comprising respiratory hose and an electric heating wire, as in the prior art, and automated rh controls, as in FIGS. 2 and 5–6.

FIGS. 5–6 are respective exterior and interior depictions of assembly 32. FIG. 5 shows housing 33 as covering components of sensor 31 and conventionally mounted on an outer, normally-upward aspect of wye 14. FIG. 6 shows interior aspects of the assembly; in particular, wall portions defining airway 15, the sensor socketed in wye 14, and probe 34 extending into the airway at a station within the wye and proximate the delivery end of conduit INS. For a circular airway with diameter of, say, 0.6 inch or 15 mm. at the station, the probe would extend into the airway by, say, 0.25 inch or 7 mm. Substances AER in down-path movement in the airway present to the probe. Again, dimensionally or otherwise, the probe should in no way impede free passage of substances in the airway.

Assembly 32 may well be a distinct article of manufacture or commerce. The assembly—and, particularly, its wall portions defining airway 15—is adapted to connect with and disconnect from the delivery end of conduit INS and, when and as connected, to communicate with the conduit, and to extend the inspiratory flow path through the airway and wye 14.

Circuit 2 operates on the same principle as circuit 1, that is, circulation of heated water 30 in tube 11 serves to transfer heat to substances AER in the distal hoses, and confers at least one of the noted benefits or advantages. In terms of intra-conduit environment, this heating is to provide the substances in near-saturated condition—say, at rh=95%—in conduit INS and airway 15.

With further reference to the automated controls in circuit 2, sensor 31 is a low voltage solid state electronic device for sensing or detecting rh (water vapor). IC humidity sensor #IH-3605, supplied by HY-CAL Engineering, 9650 Telstar Avenue, El Monte, Calif., is an exemplary such device. It measures rh as a function of electrical capacitance as influenced by substances presenting at its probe. With applied voltage of 5 volts dc and current requirement of 200 microamperes, it generates a substantially linear signal with outputs from 0.8 to 3.9 volts dc for sensed rh over the 0–100% rh range, and is suitable from the electrical safety standpoint.

Controller 35 is conventionally adjustable with reference to the signal from sensor 31, that is, within a range of set-points corresponding to signal outputs, and to the set-point corresponding to the output of a selected, desired or established rh level. Cable 36 is connectible with each of and extends between the sensor and the controller, and implements the controller to receive the signal. Preferably, the signal is subject to signal conditioning so that any particular sensor may be utilized with any particular controller.

Controller 35 controls pump 29 for circulation/non-circulation of heated water 30 in response to signal outputs of sensor 31. For example, when the selected, desired or established set-point is 95% rh, and the output signals sensed rh above the 95% level, the controller by electrical means actuates or maintains the pump in active status to circulate heated water to tube 11 and thereby to provide one or more of the noted benefits and advantages. Limitations in the accuracy of sensor technology are such that at the 95% rh set-point, rh in the range of 93–100% as sensed by the sensor is satisfactory. When output indicates rh level lower than than 95%—that is, below near-saturation—substances AER in conduit INS yet have capacity to retain water vapor, condensate is unlikely to form, and the controller leaves the pump inactive. The controller may, as well, electrically control heater 21.

Circuit 2 includes conventional electrical and electronic components with power connections, sources and other means to serve and operate its several components. With conventional fitments and meters, optionally including sensor 31, but without controller 35, other components of circuit 2 may operate under manual controls.

Additional Safety Considerations for Circuits 1–2

In the interests of safety and good practice for heating-tube breathing circuits like circuits 1–2, circulation of water 30 by pump 29 is preferably by aspiration rather than under positive pressure. Aspiration inter alia minimizes stress on tube 11 and obviates possibility of injection of pressurized water into a conduit in case of tube or other failure. Such circuits and device 4, may include low- or add-water indicators (for example, to restore evaporation losses) and temperature controls for water in reservoir 13, with warning and shut-off features if the temperature exceeds, say, 170° F., the reservoir becomes dry, or power fails.

Accessories for Circuits 1–2

FIGS. 7A–7B respectively illustrate clip 51 and strut 52 as two exemplary accessories of which either, as and if needed, may be utilized for or with reference to tube 11. Clip 51, in FIG. 7A, is accommodating or assuring a relatively sharp turn or bend in the tube. The clip's wall portions form an obtuse or right angle, and each is generally tubular but with a slot or lengthwise interruption. A short portion of the flexile heating tube—as FIG. 7A presents in phantom, and with a bend—may be "snapped" into or otherwise retained within the the clip.

FIG. 7B shows strut 52 which, in an inspiratory or expiratory conduit, may space tube 11 from and in concentric relationship with the conduit wall. The strut has central ring 53 defining aperture 54 and at least two of arms 55 extending outwardly from the ring. The tube may be received in the aperture. The arms are sized to extend to the conduit wall. Preferably, as shown, the arms are radial, of equal length, and equally angularly spaced.

Both clip 51 and strut 52 are comprised of thin members—with thickness of less than, say, 0.03125 inch to offer minimal resistance to aeriform substances, and the axial dimension of the strut need not exceed, say, 0.25 inch of 6.25 mm. Clip and strut are, preferably, of plastic material so not appreciably to take heat from the substances or tube, or to afford surfaces for condensate formation.

Circuit 3

FIG. 8 discloses circuit 3 in which assembly 32 and controller 34, as in circuit 2 (see FIGS. 3 and 5–6), are utilized to control rh in hose 37 which is fitted with wire 38 to heat the hose and substances AER therein. This hose comprises an inspiratory conduit and defines an inspiratory flow path (like conduit INS in circuit 2), and the hose, the wire, and connector 39 may be the same as components depicted in FIG. 3 of said U.S. Pat. No. 5,357,948.

In circuit 3, as shown, assembly 32 is connected with the delivery end of hose 37 and, again, cable 36 connects sensor 31 with controller 35.

Assembly 32 and controller 35 function with reference to wire 38 generally as do the same components with reference to tube 11 in circuit 2. That is, when sensor 31 makes a signal with output indicating a sensed rh level above the selected set-point, the controller, in response to the signal, supplies heating by electrically-implemented means. Specifically, the controller—by, for example, closing a switch, reducing resistance or other suitable action—allows electric current to heat the wire. This heat transfers to aeriform substances in the hose, and confers one or more of the noted benefits and advantages.

Components such as assembly 32 and controller 35 are likewise suitable for a circuit with an electric wire disposed within a conduit for heating aeriform substances there.

Methods

This invention includes methods for control of humidity of aeriform substances in a conduit of a breathing circuit and to inhibit formation of condensate from the substances in a said conduit, including methods I and II, as described. Method I confers or relates to a capability so to inhibit or control unwanted condensate, and includes steps of (a) fitting a tube to receive and contain heated liquid, and (b) installing a portion of the tube within at least the inspiratory conduit, so that, when heated liquid is supplied to the tube, heat may transfer from the liquid and across said portion to the substances. Step (a) of method I, for example, covers activities needed prior to step (b) such as selecting suitable tube material, arranging suitable tube length and adapting ends of the tube for connection with the source of heated liquid.

Additional or optional steps relating to method I, and actually to employ said capability are (c) providing a source of the heated liquid, and (d) supplying heated liquid from the source to the tube.

A subsequent related step is (e) circulating the supplied liquid through the tube and between the tube and the source.

Method II concerns humidity control for a breathing circuit which has an enclosed inspiratory flow path with a delivery end, heating means for the flow path and aeriform substances in movement on the path. The heating means may be a heated-liquid heating tube such as tube 11; or, an electrical heating wire on or in respiratory hose such as wire 38 on hose 37.

Method II includes steps of (f) establishing an rh level for aeriform substances as to be delivered to the patient, (g) sensing rh levels of the substances proximate the patient, (h) generating a signal indicative of sensed rh level, and (j) providing heat to the substances in response to a signal indicative of sensed rh level above the selected level.

For purposes of step (f), the level to be established may be a near-saturation level, say, rh=95%. Method II may include, in step (g), monitoring rh level of the substances on a continual basis or for the whole period while the method is being practiced; and, in step (j), providing heat, more specifically, by circulating heated liquid in a heating tube or by supplying electric current to the electrical heating wire.

Apart from the several embodiments and circuit elements and components and methods described in this specification, other breathing circuits—including those with interior heating means, a common wall between discrete inspiratory and expiratory channels, or course-reversal means for an inter-conduits heating tube—as well as other methods for non-electric or liquid-based heat exchange and humidity controls with reference to breathing circuits are within the spirit and scope of this invention.

What is claimed is:

1. A breathing circuit of a respiratory device with inspiratory and expiratory conduits providing a flow path and with the improvement comprising a heating tube within a portion of each conduit, and a manifold including a cross member defining exterior wall portions, and an interior wall within the exterior wall portions, said interior wall being a common wall for the conduits, and defining a port in the common wall for transit of the heating tube from one conduit to the other conduit;

an inspiratory side portion on the cross member and defining walls for the inspiratory conduit and up-path and down path openings; and, an expiratory side portion on the cross member and defining walls for the expiratory conduit and up-path and down-path openings.

2. A breathing circuit according to claim 1 wherein each conduit comprises a first hose and a second hoses, the inspiratory side portion is intermediate the first and second hoses of the inspiratory conduit, and the expiratory side portion is intermediate the first and second hoses of the expiratory conduit.

3. A breathing circuit, for transit of an humidified aeriform substance, comprising wall portions defining an inspiratory channel for aeriform substances, an expiratory channel for aeriform substances, a common wall between between the channels and an inter-channels port in the common wall; and, a tube to receive a heated liquid, and whereof a portion of the tube extends within the wall portions and there is exposed to a least a part of each of the inspiratory and expiratory channels, and transits the common wall via and occupies the inter-channels port;

so, when the portion of the tube receives a heated liquid at temperature substamtially higher than the temperature of an humidified aeriform in one of the channels, heat from the heated liquid transfers across the portion of the tube to provide heating to the humidified aeriform substance in one of the channels with at least one of these effects: a compensatory effect for heat loss the humidified aeriform substance may otherwise sustain, enhanced capacity of the humidified aeriform substance to retain water vapor, and an intra-channel environment tending to inhibit formation of condensate from the humidified aeriform substance.

4. The breathing circuit of claim 3 where the tube is to receive heated water, the circuit includes a source for heated water, the wall portions define a port to the inspiratory channel and a port from the expiratory channel, and the tube is arranged for circulatory relationship with the source for heated water and transits the ports.

5. The breathing circuit of claim 4 where the source for heated water comprises a reservoir and a water heater for the reservoir, and the reservoir and the heating tube comprise a containment for the water.

6. A breathing circuit for a pulmonary ventilator, for controlling condensate from an humidified aeriform substance in transit of the circuit, and comprising a wye with inspiratory and expiratory airways each in communication with a common airway;

wall porttions defining a first conduit providing an inspiratory flow path and In communication with the wye at the inspiratory airway, a second conduit in communication with the wye at the expiratory airway and providing an expiratory flow path, and an inter-conduits course;

a source of heated liquid;

a tube arranged for communication with the source of heated liquid, to receive heated liquid from the source and with a portion of the tube extending interiorly of a part of the first conduit, along the inter-conduits course, and of a part of the second conduit, and is there exposed to each flow path;

so when the portion of the tube receives from the source heated liquid at temperature substantially higher than the temperature of an humidified aeriform substance on at least one of the flow paths, heat from the heated liquid transfers from the tube and to provide heating to the humidified aeriform substance to compensate for heat losses the humidified aeriform substance may sustain in connection with the transit, to enhance the capacity of the humidified aeriform substance to retain water vapor, and to contribute to an intra-conduit environment tending to inhibit formation of condensate from the humidified aeriform substance.

7. The breathing circuit of claim 6 where the source of heated liquid is a source of heated water comprising a reservoir for heated water and a water heater for water in the reservoir; the circuit includes a pump; the wall portions provide a common wall between the conduits; the common wall defines the inter-conduits course and an inter-conduits port; the tube is in circulatory relationship with the reservoir and transits the common wall via and fully occupies the inter-conduits port; and, the pump serves for circulating water in the tube and between the reservoir and the tube.

8. A breathing circuit for a respiratory device, for controlling condensate from humidified aeriform substances in transit of the circuit, and comprising an aeriform-substances exchange member including a wye with first and second airways each in communication with a third airway, and wall portions defining a first conduit with an inspiratory floe path in communication with the wye at the first airway, a second conduit in communication with the wye at the second airway and with an expiratory flow path, and an inter-conduits course, and whereof each conduit includes, relative to the wye, a distal hose and a proximal hose;

a reservoir for a heated liquid, and including a heater and a pump; and, relative humidity controls including a tube arranged in circulatory relationship with the reservoir and with a part of a part of the tube disposed within the distal hose of the first conduit, along the inter-conduits course, and within the distal hose of the second conduit, and exposed to the flow path in each distal hose;

a sensor in communication with the first airway and fitted to sense relative humidity in the first airway and to emit an electric signal indicating when relative humidity is above an established level; and, a controller to activate the pump in response to the electric signal;

so, when a heated liquid is in the reservoir, an humidified aeriform substance is in the first conduit and the first airway, and the sensor emits the electric signal, then the controller activates the pump to circulate the heated liquid between the reservoir and the tube, and heat transfers from the heated liquid across the part of the tube and to provide heating to the humidifieid aeriform substance and to reduce the relative humidity of the humidified aeriform substance.

9. The breathing circuit of claim 8 where the distal hose of the first conduit defines an up-path port, the distal hose of the second conduit defines a down-path port, some said wall portions define a manifold intermediate the conduits and proximate the wye, the manifold defines the inter-conduits course and an inter-conduit port, and the tube transits each said port.

10. The breathing circuit of claim 9 where the manifold has substantially rigid wall portions, has a generally tubular inspiratory side, a generally tubular expiratory side, and a generally tubular member intermediate the sides, the sides are generally parallel, and the transverse member defines an interior common wall and the common wall defines the inter-conduits port.

11. A breathing circuit for a respiratory device comprising a patient interface including an inspiratory airway, respiratory hose with wall portions defining an inspiratory conduit in communication with the inspiratory airway, and with an electrical heating wire for heating the inspiratory conduit and a respiration-related aeriform substance in the conduit, and automated controls to monitor relative humidity of a said substance in the conduit including a sensor on the interface, comprising a probe, and fitted to sense relative humidity of a said substance in the inspiratory airway and as presenting at the probe, and to make an electric signal indicative of a sensed level of relative humidity of a said substance, and a controlled to allow, in response to the signal, electric current to flow to and to heat the wire and a said substance in the conduit when the sensed level of relative humidity exceeds an established level of relative humidity.

* * * * *